(12) United States Patent
Giambattista et al.

(10) Patent No.: US 10,188,798 B2
(45) Date of Patent: Jan. 29, 2019

(54) MEDICAMENT DELIVERY DEVICE

(71) Applicant: SHL GROUP AB, Nacka Strand (SE)

(72) Inventors: Lucio Giambattista, East Hanover, NJ (US); Antonio Bendek, Vernon, NJ (US)

(73) Assignee: SHL GROUP AB, Nacka Strand (SE)

( * ) Notice: Subject to any disclaimer, the term of this patent is extended or adjusted under 35 U.S.C. 154(b) by 0 days.

(21) Appl. No.: 14/878,159

(22) Filed: Oct. 8, 2015

(65) Prior Publication Data
US 2016/0022908 A1 Jan. 28, 2016

Related U.S. Application Data

(63) Continuation of application No. 13/139,344, filed as application No. PCT/EP2009/065911 on Nov. 26, 2009, now Pat. No. 9,186,458.
(Continued)

(30) Foreign Application Priority Data

Dec. 12, 2008 (SE) ...................................... 0850133

(51) Int. Cl.
*A61M 5/20* (2006.01)
*A61M 5/31* (2006.01)
(Continued)

(52) U.S. Cl.
CPC ......... *A61M 5/2033* (2013.01); *A61M 5/3157* (2013.01); *A61M 5/326* (2013.01);
(Continued)

(58) Field of Classification Search
CPC .. A61M 5/2033; A61M 5/3157; A61M 5/326; A61M 2005/2013;
(Continued)

(56) References Cited

U.S. PATENT DOCUMENTS 5,244,465 A * 9/1993 Michel ................... A61M 5/24
604/187
5,271,527 A 12/1993 Haber et al.
(Continued)

FOREIGN PATENT DOCUMENTS

DE 10229122 2/2004
WO WO 9626754 A2 * 9/1996 ........ A61M 5/31551
(Continued)

OTHER PUBLICATIONS

International Search Report for Int. App. No. PCT/EP2009/065911, dated Jul. 8, 2010.

*Primary Examiner* — Lauren P Farrar
(74) *Attorney, Agent, or Firm* — McDonnell Boehnen Hulbert & Berghoff LLP

(57) ABSTRACT

The present invention relates to a medicament delivery device comprising a housing having opposite distal and proximal ends; a medicament container holder with a medicament container, disposed within the housing, wherein the container has a front opening with or for a delivery member for delivering the medicament therethrough and at least a movable stopper; a drive unit comprising a power source and a plunger rod, wherein said drive unit is arranged to be movable between a non-delivery state in which said power source is in a cocked state and a delivery state in which said power source acts on said plunger rod which in its turn acts on said stopper for delivering a dose of medicament from said medicament container; retaining means operably connected to said drive unit, and capable of holding said drive unit in its non-delivery state; and activation means operably connected to said retaining means, and capable of releasing said drive unit from its non-delivery state; wherein the device further comprises a delivery indication mechanism comprising a flexible band arranged with different indications, guide means arranged on the inner surface of the (Continued)

housing for storing and guiding said band, and an opening in said housing through which said indications are visible; wherein said band comprises a first end connected to said drive unit such that when said drive unit is released from its non-delivery state, said band moves through said guide means.

10 Claims, 4 Drawing Sheets

Related U.S. Application Data

(60) Provisional application No. 61/122,373, filed on Dec. 13, 2008.

(51) Int. Cl.
*A61M 5/32* (2006.01)
*A61M 5/315* (2006.01)

(52) U.S. Cl.
CPC .............. *A61M 2005/2013* (2013.01); *A61M 2005/3125* (2013.01); *A61M 2205/583* (2013.01); *A61M 2205/584* (2013.01)

(58) Field of Classification Search
CPC .... A61M 2005/3125; A61M 2205/583; A61M 2205/584
See application file for complete search history.

(56) References Cited

U.S. PATENT DOCUMENTS

| 6,221,046 | B1 | 4/2001 | Burroughs et al. |
| 8,366,668 | B2 * | 2/2013 | Maritan ............. A61M 5/2033 604/135 |
| 2004/0097883 | A1 | 5/2004 | Roe |
| 2005/0277886 | A1 * | 12/2005 | Hommann ......... A61M 5/2033 604/136 |
| 2010/0168677 | A1 | 7/2010 | Gabriel et al. |

FOREIGN PATENT DOCUMENTS

WO 01/87386 11/2001
WO 2004/020028 3/2004

* cited by examiner

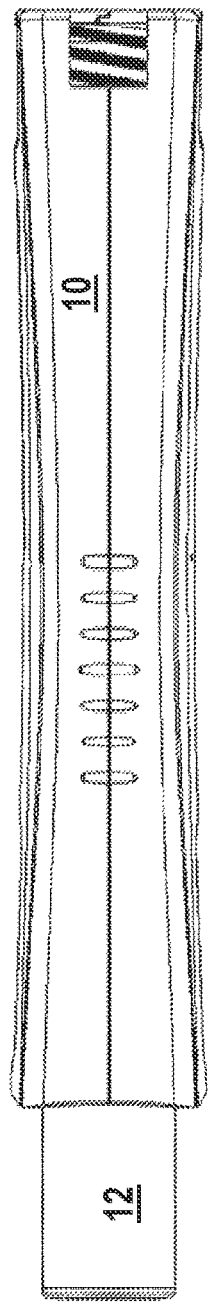
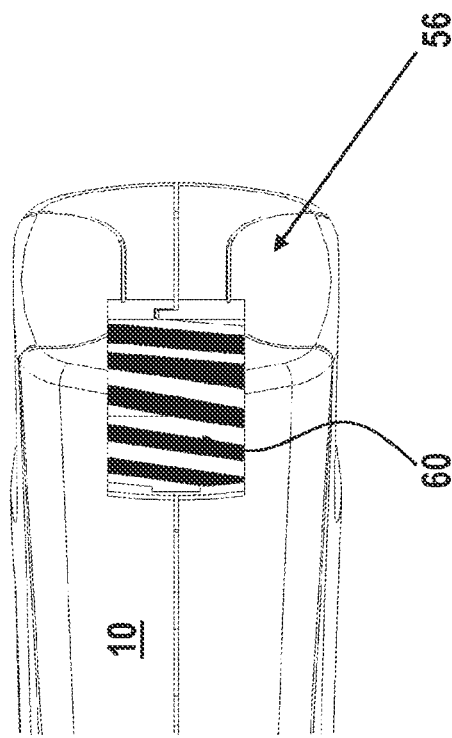
Fig. 1a
Fig. 1b

MEDICAMENT DELIVERY DEVICE

CROSS REFERENCE TO RELATED APPLICATIONS

The present application is a continuation of U.S. patent application Ser. No. 13/139,344, filed Oct. 31, 2011, which is a U.S. National Phase Application pursuant to 35 U.S.C. § 371 of International Application No. PCT/EP2009/065911 filed Nov. 26, 2009, which claims priority to SE Patent Application No. 0850133-0 filed on Dec. 12, 2008, and also claims priority to U.S. Patent Application No. 61/122,373 filed on Dec. 13, 2008. The entire disclosure contents of these applications are herewith incorporated by reference into the present application.

TECHNICAL AREA

The present invention relates to a medicament delivery device and in particular a medicament delivery device comprising a medicament delivery indication means.

BACKGROUND

Devices for the delivery of medicament in an automatic way e.g. auto-injectors, are known as convenient and safe aids for patients to administrate various drugs themselves. For safety reasons, many devices for the delivery of medicament include covers and other devices that protect users before and after use, for example, from an injection needle. Although different devices for the delivery of medicament vary in their total feature sets, they all have a mechanism that delivers the contents of a preloaded, prefilled container automatically, i.e., without requiring a person to manually force the contents within a container through a delivery member e.g. a needle, a nozzle, into the patient.

One problem associated with self-administration of medicament with injectors that perform the injection automatically is how the user could know when the injection is completed and it is safe to remove the injector from the injection site. This is a non-negliable problem because many drugs need to be injected in rather precise doses and if the injector is removed to soon, a part of the dose may be expelled outside the body of the patient. It could also be that the dose needs to be injected at a certain depth in the skin of the patient, and if the injector is removed prematurely a part of the dose may be injected into the skin during withdrawal, i.e. at lesser depths.

There have been certain attempts to alert or indicate to the user when the injection is completed. U.S. Pat. No. 6,221,046 describes an injection device having an "end of injection click" including an extension on a flexible tab of a dose dial mechanism. The tab with the extension falls into a groove in the housing, causing an audible click at the end of injection. US 2004/0097883 discloses a similar end of injection click solution.

Other solutions include indicators that are moved during injection. One such device is disclosed in US 2005/0277886 where an indicator is connected to an intermediate part in an injector such that the indicator only moves or is visible, during a second distance of a total movement distance of a plunger rod, where the total movement distance includes a first penetration distance and second injection distance.

The above solutions are not optimal in all aspects. The audio information may be lost if the device is used in a noisy environment and the click of a tab falling into a groove may not be heard even in rather quite environments. The mechanical indicator solution entails a number of extra components which makes the injector more complicated and more expensive. Further the indicator according to US 2005/0277886 is visible on the side of the injector which is not an ideal place since the user has to be certain when using the device that the hand grip does nor cover the indicator.

SUMMARY

The aim of the present invention is to remedy the above mentioned drawbacks and to provide an indication mechanism that reliably and positively provides information to the user that a medicament delivery is in progress and when it is completed, which indication mechanism does not add many features or components to the device.

This aim is obtained according to the present invention by a medicament delivery device comprising the features of the independent patent claim.

Preferable embodiments of the invention form the subject of the dependent patent claims.

According to a main aspect of the invention it is characterised by a medicament delivery device Medicament delivery device comprising a housing having opposite distal and proximal ends; a medicament container holder with a medicament container, disposed within the housing, wherein the container has a front opening with or for a delivery member for delivering the medicament therethrough and at least a movable stopper; drive unit comprising a power source and a plunger rod, wherein said drive unit is arranged to be movable between a non-delivery state in which said power source is in a cocked state and a delivery state in which said power source acts on said plunger rod which in its turn acts on said stopper for delivering a dose of medicament from said medicament container; retaining means operably connected to said drive unit, and capable of holding said drive unit in its non-delivery state; and activation means operably connected to said retaining means, and capable of releasing said drive unit from its non-delivery state; wherein the device further comprises a delivery indication mechanism comprising a flexible band arranged with different indications, guide means arranged on the inner surface of the housing for storing and guiding said band, and an opening in said housing through which said indications are visible; wherein said band comprises a first end connected to said drive unit such that when said drive unit is released from its non-delivery state, said band moves through said guide means.

According to another aspect of the invention, the indications are a start indication for informing the user that the device is ready for a medicament delivery, a progress indication for informing the user that the medicament delivery is in progress, and a final indication for informing the user that the medicament delivery has come to an end.

According to a further aspect of the invention, different colours are used as indications.

According to yet another aspect of the invention, said progress indication comprises lines.

According to yet a further aspect of the invention, the first end of the band is connected to a distal end of the plunger rod.

According to another aspect of the invention, the start indication is shown through the opening when the drive means is in the non-delivery state, wherein the progress indication is shown through the opening during the movement of the drive means from the non-delivery state to the delivery state, and wherein the final indication is shown through the opening when the movement of the drive means has come to an end.

According to a further aspect of the invention, the opening is placed in the transition between a side surface and a distal end surface of the housing.

According to another aspect of the invention, the guide means are arranged on the inner surface of the housing at the distal end of the housing.

According to yet another aspect of the invention, the device is an injector.

There are a number of advantages with the present invention. The use of a flexibleband connected to the plunger rod provides a very simple solution with very few components, where the band provides the possibility of placing the delivery indication in many different locations on the housing of the device. The guide means further facilitates the placing of the band at appropriate places. Thus it is possible to have the indication opening or window at the distal end of the device, which is not possible with most mechanical indicators connected to the drive unit.

The band is preferably arranged with indications that are easily observable to a user and that give clear indications that the delivery is in progress. Thus different colours could be used that provide a moving action of the indication when passing the window. Further there could be a different set of indications when the delivery is coming to an end in order to clearly indicate to the user that the delivery device could be removed. The user is thus provided with full information regarding the function of the device and any premature withdrawal of the device is minimized.

These and other aspects of and advantages with the present invention will become apparent from the following detailed description and from the accompanying drawings.

BRIEF DESCRIPTION OF THE FIGURES

In the following detailed description of the invention, reference will be made to the accompanying drawings, of which FIG. 1a is side view of a medicament delivery device according to the present invention, FIG. 1b is a detailed view of the medicament delivery device of FIG. 1a, FIG. 2 is a side view in cross-section of the medicament delivery device of FIG. 1 in an initial state.

DETAILED DESCRIPTION

Figure 2:
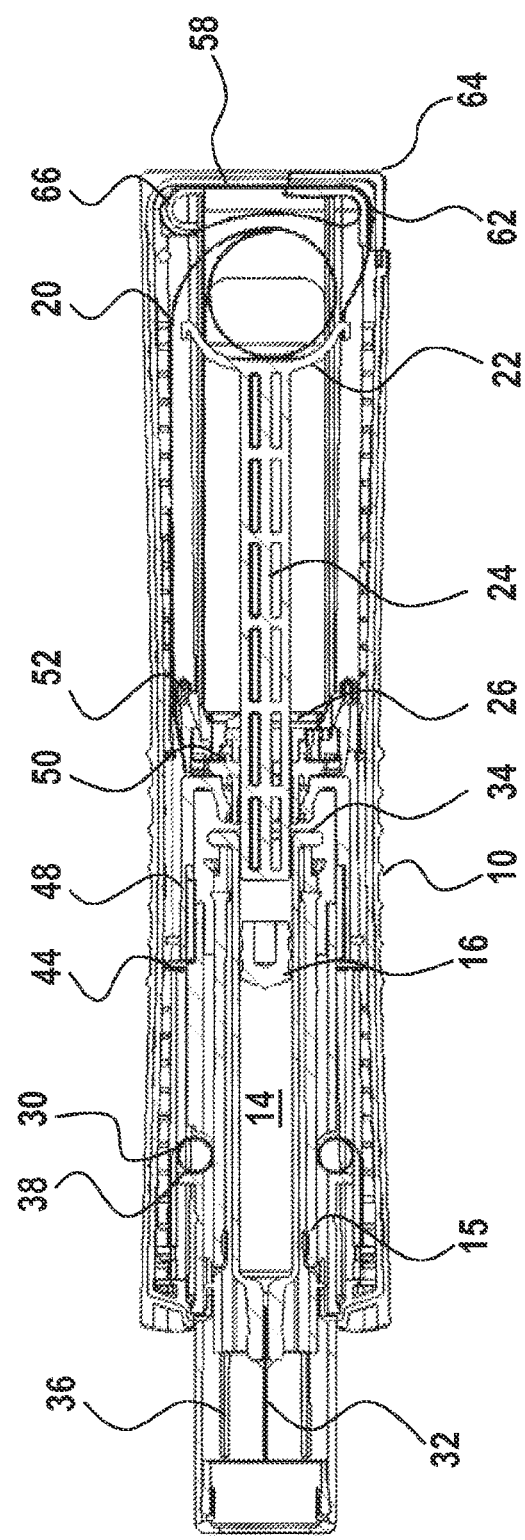

In the present application, when the term "distal part/end" is used, this refers to the part/end of the delivery device, or the parts/ends of the members thereof, which under use of the delivery device, are located the furthest away from the medicament delivery site of the patient. Correspondingly, when the term "proximal part/end" is used, this refers to the part/end of the delivery device, or the parts/ends of the members thereof, which under use of the delivery device, are located closest to the medicament delivery site of the patient.

The medicament delivery device of the present invention relates a medicament delivery device comprising a housing 10 having opposite distal and proximal ends; a medicament container holder 15 with a medicament container 14, disposed within the housing, wherein the container has a front opening with or for a delivery member for delivering the medicament therethrough and at least a movable stopper 16; a drive unit comprising a power source 20 and a plunger rod 24, wherein said drive unit is arranged to be movable between a non-delivery state in which said power source is in a cocked state and a delivery state in which said power source acts on said plunger rod which in its turn acts on said stopper 16 for delivering a dose of medicament from said medicament container 14; retaining means 26 operably connected to said drive unit, and capable of holding said drive unit in its non-delivery state; and activation means 36, operably connected to said retaining means, and capable of releasing said drive unit from its non-delivery state; wherein it further comprises a delivery indication mechanism 56 comprising a flexible band 58 arranged with different indications 60, guide means 62, 67 arranged on the inner surface of the housing for storing and guiding said band, and an opening 64 in said housing through which said indications are visible; wherein said band comprises a first end connected to said drive unit such that when said drive unit is released from its non-delivery state, said band moves through said guide means.

The indications are a start indication for informing the user that the device is ready for a medicament delivery, a progress indication for informing the user that the medicament delivery is in progress, and a final indication for informing the user that the medicament delivery has come to an end.

The embodiment of the medicament delivery device shown in the drawings is in the form of an injection device, but it can also be an inhaler or other type of medicament delivery device. As seen in the figures, a cap 12 is mounted in the proximal end of the housing; the container 14 is of the syringe type having adapted a delivery member, e.g. an injection needle 32, FIG. 2.

The power source, which is shown in the embodiment, is a coil spring of band material 20 as e.g. a constant force spring, a negative gradient force spring, but it s not limited to such a spring. It can also be e.g. a spiral spring, a gas spring, a motor or the like arranged to be in a cocked state wherein accumulated energy is stored. The power source is connected in a known manner to the plunger rod.

The retaining means 26 comprises a latch releasably connected in a known manner to the plunger rod for retaining said drive unit in its non-delivery state.

The activation means comprises a needle shield 36 or alternatively a button slidably positioned through the housing, operably connected to said retaining means for releasing said drive unit from its non-delivery state, upon actively operation by an user, such that said accumulated energy stored in the power source is transferred to the plunger rod for driving the stopper a predetermined distance whereby the medicament within said container is expelled, The activation means further comprises at least one resilient means 30 which function will be described below.

In the embodiment shown, the container 14 comprises an injection needle, in its proximal end and the cap 12 comprises a shield for protecting the injection needle. Moreover, the container 14 preferably comprises a flange 34 at its distal end which abuts a periphery surface of the container holder for preventing movement of the container.

The needle shield 36 is arranged as a tubular member wherein a proximal portion of said tubular member extends outside the housing 10 towards the proximal end of the device substantially covering the delivery member when the drive unit is in its non-delivery state. An outwardly annular ledge 38 extending radially from the distal end of the tubular member is arranged abutting a ledge on the inner surface of the housing when the drive unit is in its non-delivery state. Further, the tubular member also comprises tongue extensions 48 extending towards the distal end of the device.

In the embodiment of the device shown at least one resilient means 30, e.g. two coil springs, is arranged. These springs can also be replaced by another kind of resilient means e.g. a spiral spring. The wound ends of the spring 30 are cradled within the outwardly annular ledge 38 extending radially from the distal end of the tubular member and the other end of the spring is secured to a fixed point on the inner surface of the housing.

The proximal end of the plunger rod 24 is arranged to be in contact with the stopper 16 inside the container and the distal end the plunger rod comprises a carrier 22 which is formed as a saddle for cradling the wound end of the power source 20. The other end of the power source is secured to a holder 52 which is fixedly arranged to inner surface of the housing 10. The retaining means 26 is pivotally arranged to the holder 52 and comprises a protrusion arranged to be in contact with a groove of the plunger rod for holding the drive unit in the non-delivery state. The holder also comprises a through hole for allowing the plunger rod to pass through.

According to the invention, the delivery indication mechanism 56 is arranged inside the housing. The band 58 being of a flexible yet generally non-resilient material is arranged with different indications or indicia 60, which will be described in more detail below. The first end of the band is attached to the carrier 22 of the plunger rod and the other end of the band is unattached. The band is arranged around the guide means 62, 66 which form a slit on the inner end surface of the housing wherein the band is stored and through which the band runs. As seen from FIG. 1b, the opening/window 64 is preferably placed in the transition between a side surface and a distal end surface of the housing, and the guide means 62, 66 are preferably arranged at the distal end of the housing, FIG. 2.

Before use, as seen in FIG. 2, the cap 12 is removed from the device. The delivery device is now ready to be used. Through the opening/window 64 is shown the start indication which informs the user that the device is ready for delivery. The tubular member 36 is pressed against a delivery site, e.g. a needle penetrates into the delivery site a predetermined depth, and whereby the wound end of the springs 30 rotates in the outwardly annular ledge 38 as the springs unravels. This movement is sufficient to displace the tongue extensions 48 towards the distal end of the device for pushing and thereby pivoting the retaining means 26. The pivoting of the retaining means 26 causes its protrusions to come out of contact from the groove arranged on the plunger rod 24. The plunger rod is urged forwardly as the wound end of the power source 20 rotates within the saddle 22 of the plunger rod. The plunger rod now urges the stopper 16 inside the container 14 towards the proximal end of the device as fluid is expelled from the container through the delivery member.

Figure 3:
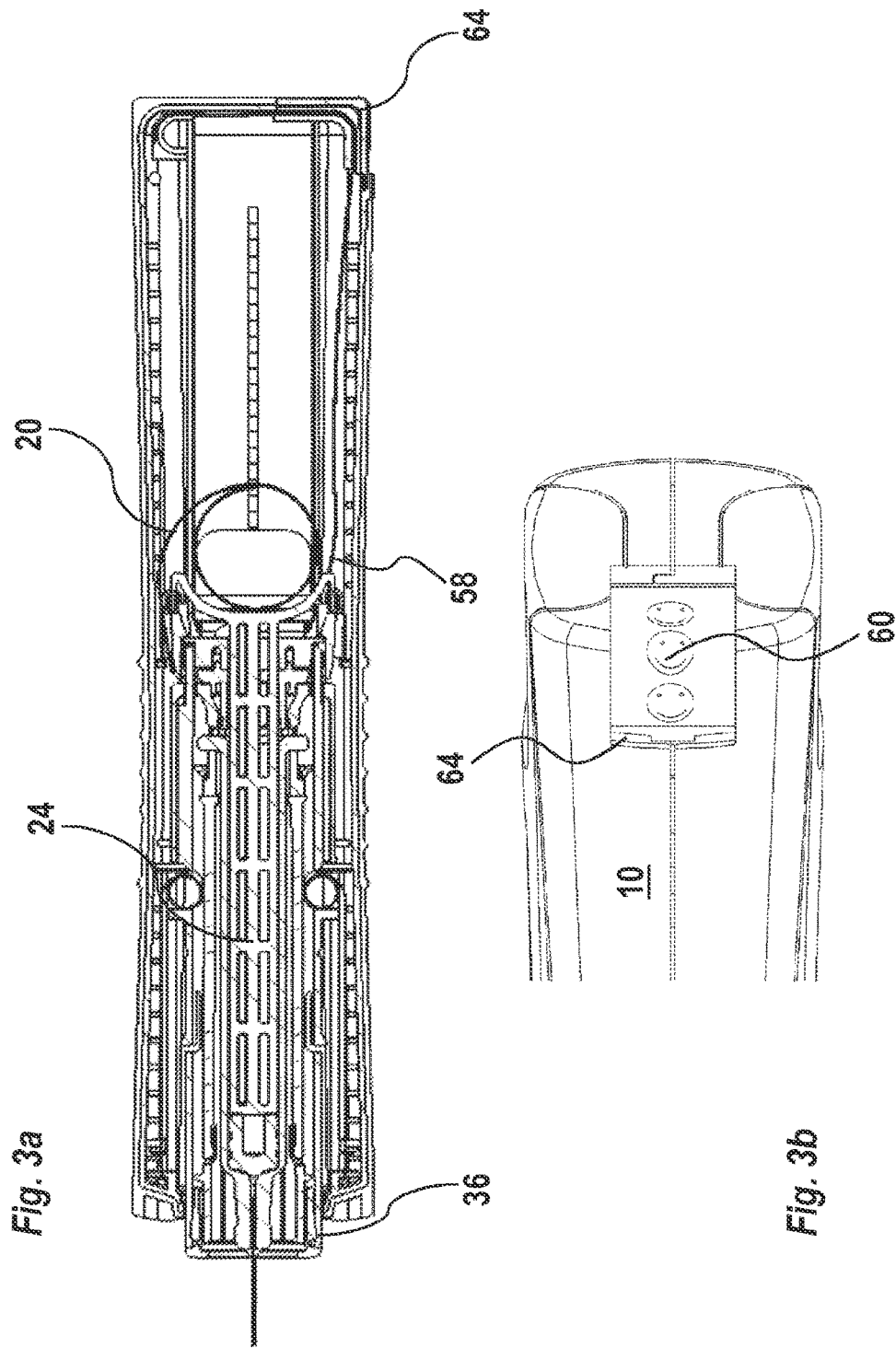
FIG. 3a is a side view in cross-section of the medicament delivery device of FIG. 1 after completed delivery.
FIG. 3b is a detailed view similar to FIG. 1b.

During the delivery sequence, according to the present invention, the plunger rod 24 and the carrier 22 move downwards due to the force of the power source 20. Because of the attachment of the band 58 to the carrier 22, the band will be pulled through the guide means 62, 66 whereby the progress indication on the band will pass the opening/window 64. The moving pattern of the progress indications or indicia passing the window 64 is a positive and reliable indication that the delivery is in progress. As an example of indications, as shown in FIG. 1a, they could consist of lines of alternating dark and light colours, such as black and white, and positioned at an angle to the direction of movement. With this configuration the movement and thus delivery sequence is clearly visible through the opening/window 64. When the delivery sequence has come to an end, this could be indicated by the final indication. One example of the final indication is shown in FIG. 3b, where smiling faces are shown, which is a positive indication that the delivery is completed, and that the device may be withdrawn from the delivery site.

In this respect, it is to be understood that many types of indicia, symbols, indications and the like may be used, as well as the use of different colours, in order to indicate to the user that the delivery is in progress or has ended. The window could also be arranged with a magnifying lens for further improving the visibility of the information.

Figure 4:
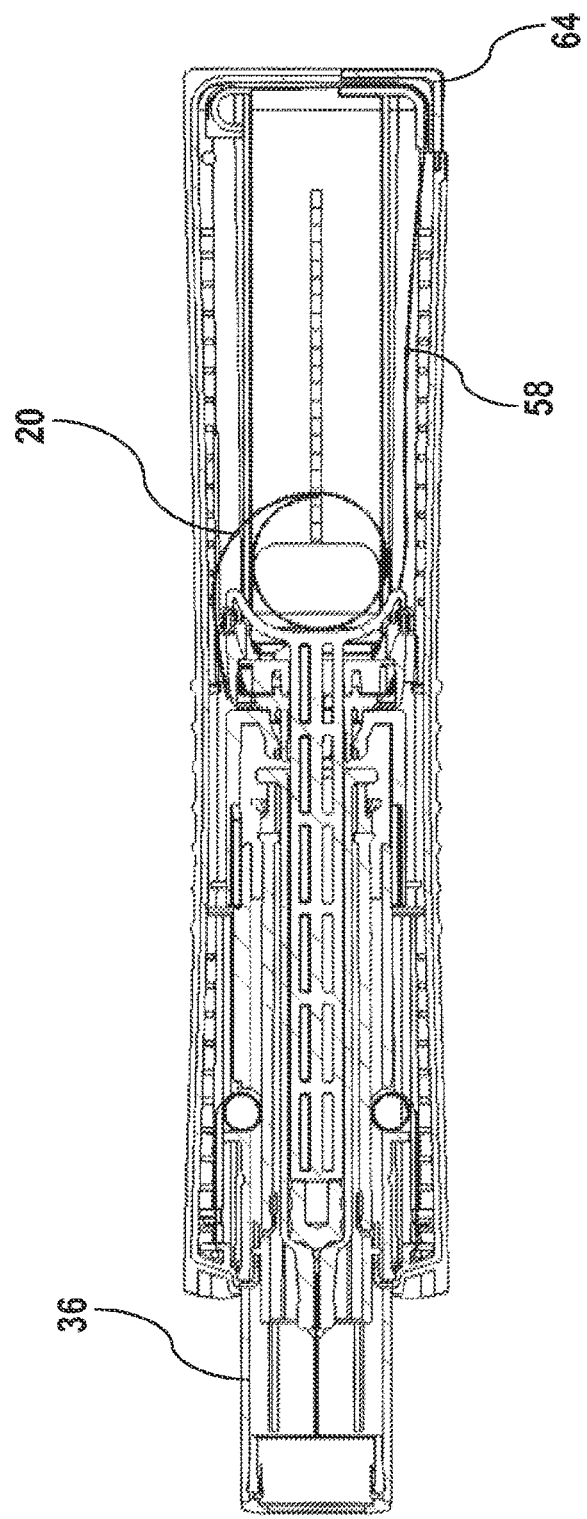
FIG. 4 is a side view in cross-section of the medicament delivery device of FIG. 1 after withdrawal from the delivery site.

Upon completion of the medicament delivery, the device is withdrawn from the delivery site and set in a final state as seen in FIG. 4. The needle shield 36 moves towards the proximal end of the device under the force of the springs 30 for covering the delivery member and the activation means is locked.

It is to be understood that the embodiment described above and shown in the drawings is to be regarded only as a non-limiting example of the present invention and that it may be amended in many ways within the scope of the patent claims.

The invention claimed is:

1. A medicament delivery device comprising:
a housing comprising a surface configured for contacting a patient's skin;
a medicament container disposed within the housing, the medicament container comprising a medicament contained behind a movable wall;
an injection needle positioned within the housing and in fluid communication with the medicament container;
a power source configured to store accumulated energy;
a plunger that moves relative to and within the medicament container immediately upon release of the accumulated energy, where the power source acts directly on the plunger such that the plunger directly contacts and moves the movable wall of the medicament container to expel medicament from the medicament container; and
an indication mechanism that is acted upon and directly moved by the plunger when the plunger moves relative to the housing and where the indication mechanism is movable only during delivery of the medicament, where the indication mechanism is not an integral part of the plunger, but is a separate component independent of the plunger and that is positioned within the housing and directly operatively associated with the plunger such that movement of the plunger directly causes separate movement of the indication mechanism only during delivery of the medicament, where a portion of the indication mechanism is visible from outside the device housing indicating that delivery of the medicament is substantially complete.

2. The medicament delivery device of claim 1 further characterized in that the movement of the plunger directly causes motion of the portion of the indication mechanism to indicate medicament delivery progress throughout delivery of the medicament.

3. The medicament delivery device of claim 2 further characterized in that the portion of the indication mechanism rotates to indicate medicament delivery progress throughout delivery of the medicament as the plunger moves linearly when the stored accumulated energy is released.

4. The medicament delivery device of claim 1, wherein the indication mechanism provides a start indication for informing the user that the device is ready for a medicament delivery, a progress indication for informing the user that the medicament delivery is in progress, and a final indication for informing the user that the medicament delivery has come to an end.

5. The medicament delivery device of claim 4 further characterized in that the start indication, the progress indication and the final indication are arranged adjacent the opening to denote the medicament delivery progress.

6. The medicament delivery device of claim 1 wherein the housing further comprises an opening through which the portion of the indication mechanism is visible.

7. The medicament delivery device of claim 1 further comprising a button to activate the medicament delivery device, where the button is slidably positioned relative to the housing.

8. The medicament delivery device of claim 1 further comprising a needle shield that is locked into position covering the injection needle after the delivery of the medicament is substantially complete.

9. The medicament delivery device of claim 8 where the needle shield is locked when the medicament delivery device is removed from the patient's skin after the delivery of the medicament is substantially complete.

10. The medicament delivery device of claim 1 where the power source is a spring.

* * * * *